United States Patent [19]

Deckner

[11] Patent Number: 4,563,346

[45] Date of Patent: Jan. 7, 1986

[54] TOPICAL DELIVERY SYSTEM AND SKIN TREATMENT COMPOSITIONS EMPLOYING SUCH SYSTEM

[75] Inventor: George E. Deckner, Westfield, N.J.

[73] Assignee: Charles of the Ritz Group Ltd., New York, N.Y.

[21] Appl. No.: 589,283

[22] Filed: Mar. 14, 1984

[51] Int. Cl.⁴ .................. A61K 7/15; A61K 7/38; A61K 7/42; A61K 7/44
[52] U.S. Cl. .................. 424/59; 252/522 R; 424/47; 424/60; 424/68; 424/73; 514/714; 514/847; 514/859
[58] Field of Search .............. 424/47, 59, 73, 358, 424/365, 60; 514/847

[56] References Cited

U.S. PATENT DOCUMENTS

| | | | |
|---|---|---|---|
| 4,122,029 | 10/1978 | Gee et al. | 252/309 |
| 4,311,695 | 1/1982 | Starch | 424/184 |
| 4,370,319 | 1/1983 | Chapin et al. | 424/184 |
| 4,387,090 | 6/1983 | Bolich, Jr. | 424/81 |
| 4,421,769 | 12/1983 | Dixon, Jr. et al. | 424/184 |
| 4,439,416 | 3/1984 | Cordon et al. | 424/73 |

OTHER PUBLICATIONS

Davis, Cosmetics & Toiletries, 3/1980, vol. 95, pp. 87–92.
Seldner, Cosmetics & Toiletries, vol. 95, 3/1980, pp. 85 & 86.
"Information about Cosmetic Ingredients"—Dow Corning, 1982.
"Information about Volatile Silicone Fluids"—Dow Corning, 1982.
"A Formulary of Product Applications in Skin Care by Dow Corning", 1981.

Primary Examiner—Dale R. Ore
Attorney, Agent, or Firm—Lawrence S. Levinson; Burton Rodney

[57] ABSTRACT

A delivery system for delivering topically active ingredients to the skin is provided which delivery system is formed of a water-in-volatile silicone emulsion which includes an interior water phase and an exterior silicone phase which contains the active ingredient to be topically applied. A volatile silicone and a non-ionic lipophilic low HLB emulsifier are employed in forming the emulsion. The above delivery system may be employed together with active ingredients such as sunscreen agents, various topically active drugs, fragrance oils, moisturizers, anti-perspirants, humectants, and other skin care and cosmetic ingredients such as excipients, colorants, preservatives, diluents and the like.

16 Claims, No Drawings

TOPICAL DELIVERY SYSTEM AND SKIN TREATMENT COMPOSITIONS EMPLOYING SUCH SYSTEM

FIELD OF THE INVENTION

The present invention relates to a system for use in the topical delivery of active ingredients which system is formed of a thin water-in-volatile silicone emulsion using a non-ionic lipophilic emulsifier to form the emulsion, and to skin treatment compositions which employ such system to topically deliver an active ingredient.

BACKGROUND OF THE INVENTION

An ideal system for topically delivering an active ingredient should be as stable as possible and should deliver the ingredient in a manner such that it adheres to the skin for sufficient periods to obtain the required therapeutic or other benefits while other non-therapeutic components of the delivery system evaporate or are otherwise removed from the area of treatment. In an effort to develop an effective delivery system, Dow Corning has developed volatile silicone fluids, such as polydimethylcyclosiloxane, cyclomethicone and hexamethyldisiloxane, for use in formulating water-in-oil emulsions. Such emulsions are taught by Dow Corning to be useful as cosmetics solvents, to improve lubricity and spreading properties of skin creams, lotions, bath oils, and suntan, shaving and stick products and in hair grooming products such as hair sprays and conditioners. One Dow Corning product, namely, Q2-3225C, which is a dispersion of cyclomethicone and dimethicone copolyol, is said to be useful in preparing water-in-oil emulsions which are delivery systems for cosmetic ingredients such as emollients, moisturizers, sunscreens, antiperspirant salts and pigments. Furthermore, Dow Corning indicates that such emulsions feel very rich as they are applied, but quickly dry down to leave only the nonvolatile ingredients on the skin.

The stability of the Dow Corning water-in-oil emulsions containing cyclomethicone is increased by including an electrolyte in the aqueous phase, such as sodium chloride, sodium citrate, magnesium sulfate or aluminum chlorohydrate in a concentration of 1 to 3% by weight.

In preparing the Dow Corning water-in-oil emulsion, silicon block polymers, such as dimethicone copolyol, are employed as the primary emulsifier whereas Pareth-15, which is a polyethylene glycol ether of a mixture of synthetic $C_{11-15}$ fatty alcohols with an average of 3 moles of ethylene oxide, is employed as a silicone co-emulsifier.

The Dow Corning system is an excellent means for delivering only certain types of active ingredients which are compatible with the volatile silicone and the emulsifiers employed. Thus, such system may be limited in its range of acceptability of active ingredients with which it may be employed.

DESCRIPTION OF THE INVENTION

In accordance with the present invention, there is provided a delivery system for delivering topical active ingredients to the skin, which system is formed of a thin water-in-oil emulsion, usually in the form of a lotion, but which may be in the form of a thin cream, wherein the exterior silicone phase includes a volatile silicone, the active ingredient, as well as a emulsifier which is formed of a non-ionic lipophilic low HLB (hydrophilic-lipophilic balance) emulsifier. The delivery system of the invention has excellent stability and does not require an inorganic salt to stabilize the emulsion, as in the case of prior art silicon emulsions as discussed above.

Surprisingly, it has been found that silicon block polymers, such as dimethicone copolyol, which are essential in the Dow Corning system, discussed above, are not necessary and are not employed in the delivery system of the invention. Thus, the delivery system of the invention is not limited in the types of active ingredients employed as is the Dow Corning system. For example, the delivery system of the invention may be used in conjunction with fragrance oils, moisturizers, humectants, emollients, topically active drugs, other skin care and cosmetic ingredients, such as excipients, colorants, preservatives, diluents and the like.

The emulsion forming the delivery system of the invention, which will usually and preferably be in the form of a thin liquid emulsion or lotion, provide an elegant means of depositing a desired active or drug on skin. Since volatile silicone forms the external phase of the emulsion, the thin emulsions or lotions formed therewith have superior spreading properties. Traditional water/oil emulsions are perceived as having an oily or greasy feel and do not spread well on skin. Water/volatile silicone emulsions in accordance with the invention have a unique non-greasy, rich feel on application and quickly dry (the silicone and water evaporate) leaving a silky non-tacky feel on skin.

The delivery system of the invention will have a viscosity which preferably is less than 10 centipoises depending on the particle size of the emulsion formed and this may vary from a lotion to a cream. The smaller the particle size the more viscous the emulsion. Generally, the emulsion forming the delivery system of the invention will have an average particle size of less than 1 micron, depending upon the ultimate use of the emulsion and the active ingredient present therein.

The drying time of the oil-in-water delivery systems of the invention on skin can be varied using different blends of volatile silicone. Volatile silicones have extremely low surface tension and water like feel. The emulsions formed are also less likely to separate since volatile silicones have a specific gravity close to that of water.

A unique advantage and property of the system of the invention resides in that very thin water-in-oil emulsions may be formed, that is having a viscosity of less than 10 centipoises, which are susbstantially stable at 48° C. for more than 1 month. These thin emulsions contain relatively large amounts of water, for example, more than about 65% by weight. The thin emulsions of the invention may be used in normally alcohol-containing formulation such as in colognes, after-shaves, pre-shaves, skin-toners (astringents), hydrocarbon sprays and non-aerosol pump sprays and may contain 15 to 30% alcohol which is substantially less alcohol than normally used in such products. For example, conventional colognes contain up to 90% alcohol. Thus, since the above products contain less alcohol than normally found they are less flammable and cause less stinging than prior art products while providing for reduced evaporation of fragrance from the skin (due to reduced alcohol content). Furthermore, alcohol may be included in the water-in-oil systems and products of the invention without causing cream formation or separation of phases or other instability.

Use of the water-in-oil system of the invention offers the following additional advantages:

The entire emulsion of the invention is processed cold using two liquids to form the emulsion.

The delivery system of the invention is non-comedogenic (does not clog pores), exhibits a cooling effect on skin and exhibits very low irritation potential since typically less than 10% of the emulsion is left on skin.

Emulsions of the invention exhibit excellent freeze/thaw and elevated temperature stability. Emulsions of the invention also exhibit little viscosity change at temperatures up to 48° C.

Emulsion of the invention de-tackify the skin feel of many ingredients.

As seen hereinafter, many humectants exhibit much greater hydrating activity in the delivery system of the invention versus typical emulsifying systems.

The films left on the skin from the delivery system of the invention are very wash resistant and sweat resistant making this emulsion system an ideal vehicle for sunscreens. Since such emulsion system is not sticky or tacky, sand will not adhere to skin coated with such emulsion system.

In carrying out the present invention, the volatile silicone will be present in the delivery system of the invention in an amount of within the range of from about 5 to about 40% by weight and preferably from about 10 to about 25% by weight based on the total weight of the delivery system, and the non-ionic lipophilic low HLB emulsifier will be present in an amount of within the range of from about 1 to about 10% by weight and preferably from about 1 to about 5% by weight based on the total weight of the delivery system. Thus, in the oil or silicone phase, the volatile silicone will be employed in a weight ratio to the non-ionic emulsifier of within the range of from about 0.5:1 to about 40:1, and preferably from about 1:1 to about 25:1.

As indicated, an alcohol such as ethanol and/or isopropanol will be present, preferably in the silicon phase, in an amount within the range of from about 10 to about 30% and preferably from about 15 to about 25% by weight of the delivery system.

In forming the aqueous phase, water will be present in an amount of within the range of from about 40 to about 85% by weight and preferably from about 45 to about 70% by weight, based on the total weight of the delivery system.

Where the delivery system of the invention includes less than 15% by weight alcohol, a preservative may be included in an amount within the range of from about 0 to about 2% and preferably from about 0.5 to about 1.5% by weight based on the total weight of the delivery system.

Examples of volatile silicones which may be employed in the delivery system of the invention include, but are not limited to, polydimethylcyclosiloxanes, namely, cyclomethicone tetramer ($D_4$), also referred to as octamethylcyclotetrasiloxane, cyclomethicone pentamer ($D_5$), also referred to as decamethylcyclopentasiloxane, and hexamethyldisiloxane.

Non-ionic lipophilic low HLB emulsifiers which are used in the delivery system of the invention will have an HLB of less than about 7 and preferably from about 3 to about 7, and include, but are not limited to, glyceryl monoisostearate, triglyceryl diisostearate, dioleyl methyl glucaside, polyethylene glycol (22) dodecyl copolymer, triglyceryl diisostearate, sorbitan monooleate, polyglyceryl-2-sesquioleate, sorbitan diisostearate or mixtures of any two or more thereof, with glyceryl monoisostearate, triglyceryl diisostearate and dioleyl methyl glucaside being preferred.

As indicated, the delivery system may also optionally include a preservative such as methyl paraben, propyl paraben, butyl paraben, benzyl alcohol, imidazolidinyl urea, or dimethyldimethoylhydantoin and the parabens or mixtures thereof being preferred.

The delivery system of the invention is especially effective in delivering a sunscreen agent to the skin. The sunscreen, examples of which include, octyldimethyl-p-aminobenzoic acid, benzophenone-3, octylmethoxycinnamate or other category I OTC sunscreen agents will be present in the silicone phase in an amount within the range of from about 1 to about 15% based on the combined weight of the sunscreen and delivery system. As is the case with films of other active ingredients produced on skin employing the present invention, the sunscreen film produced on the skin is quite substantive, that is, will last a long time, and will not be removed by perspiration, water or by swimming, but may be removed by washing with soap.

A wide variety of active ingredients may be incorporated in the delivery system of the invention. Thus, in one embodiment of the invention, anti-perspirants, which are usually tacky, such as aluminum chlorohydroxide or other category I OTC antiperspirants may be incorporated into the silicone phase of the delivery system in an amount of within the range of from about 10 to about 30% based on the total weight of the delivery system and active ingredient and thereby made non-sticky or non-tacky.

The delivery system of the invention may include a compatible skin soothing emollient such as $C_{12}$–$C_{15}$ alcohol benzoate, dimethylsilicone fluid or phenylsilicone fluid, in an amount of within the range of from about 1 to about 5% by weight.

In a preferred embodiment, moisturizer (or humectants) such as glycerol, polyethylene glycols (for example, Carbowax 400), panthenol, sorbitol or propylene glycol may be incorporated into the water phase of the delivery system in an amount within the range of from about 0.1 to about 5% and preferably from about 0.1 to about 1%, based on the combined weight of the delivery system and active ingredient. Glycerol is the preferred moisturizer and when employed in the delivery system of the invention, hydration obtained is 2 to 3 times greater than where the other mentioned moisturizers are employed.

The resulting moisturizing composition of the invention when applied to skin produces a moisturizer film which is substantive, that is, it produces long-lasting moisturizing properties. In fact, the moisturizing film obtained lasts surprisingly longer than films produced by conventional oil-in-water emulsions.

Fragrances may also be incorporated into the silicone phase of the delivery system in an amount within the range of from about 0.1 to about 20% based on the combined weight of the fragrance and delivery system of the invention. The fragrance-delivery system of the invention when applied to skin fixes a substantive fragrance film on the skin which resists water but which can be removed by washing with soap and water. Furthermore, since processing is conducted without heat, there is no loss of fragrance during processing.

Topically active drugs, such as steroids, for example, 2-(acetyloxy)-9-fluoro-1',2',3',4'-tetrahydro-11β-hydroxypregna-1,4-dieno[16α,17-b]naphthalene-3,20-dione, 21-chloro-9-fluoro1',2',3',4'-tetrahydro-11β-hydroxypregna-1,4-dieno[16α-17-b]naphthalene-3,20-dione, (11β,16α)-9fluoro-1',2',3',4'-tetrahydro-11-hydroxy-3,20-dioxopregna-1,4-dieno[16α,17-b]naphthalen-21-oic acid, 1-methylethyl ester, or (11β,16α)-9-fluoro-11hydroxy-3,20-dioxopregna-1,4-dieno[16,17-d]cyclohexen-21-oic acid, 1-methylethyl ester, with halcinonide being preferred, may also be incorporated into the silicone phase of the delivery system of the invention in an amount within the range of from about 0.005 to about 0.6% based on the combined weight of the active ingredient and delivery system. When the steroid or other topically active drug delivery system is applied to skin, as the silicone evaporates, flux or concentration of active ingredient increases (increasing gradient) to give better skin penetration since there is more during force into the skin.

In all of the above systems, since the silicone evaporates off, it cannot interfere with the therapeutic action of the active ingredient.

Preferred delivery systems of the invention are as follows:

| Ingredient | % by Weight Based on Total System |
|---|---|
| Volatile silicone (decamethyl cyclopentasiloxane) | 10 to 25 |
| Non-ionic emulsifier (dioleyl methyl glucaside) | 1 to 5 |
| Deionized water | 45 to 70 |
| Alcohol | 15 to 25 |

The compositions of the invention are formulated, without heat, as follows.

The aqueous phase is prepared by forming a solution of deionized water, optionally a stabilizer salt and preservatives.

The oil (silicone phase) is formed by mixing volatile silicone, non-ionic emulsifier and active ingredient until homogeneous The aqueous phase is slowly added to the oil phase with high speed (preferably propeller) mixing. As the aqueous phase is added emulsification begins almost immediately. Propeller mixing is continued until an average particle size of less than 10 microns is obtained. The mixture is then pumped to a homogenizer wherein the particle size is further reduced to less than 1 micron to produce a stable emulsion or delivery system containing the active ingredient. It may then be packaged until ready for use.

The following Examples represent preferred embodiments of the present invention.

EXAMPLE 1

A stable thin water-in-oil sunscreen emulsion formulation, which includes the delivery system of the invention, having the following composition was prepared as described below.

| Ingredient | | Parts by Weight |
|---|---|---|
| (A) | Oil phase | |
| | Octyldimethyl p-aminobenzoic acid (sunscreen) | 3 |
| | Cyclomethicone (D5)-(volatile silicone) (decamethylcyclopentasiloxane) | 15 |
| | Dioleyl methyl glucaside (emulsifier) | 3 |
| | Ethyl alcohol | 20 |
| (B) | Aqueous phase | |
| | Deionized water | 76 |

The sunscreen formulation of the invention was prepared as follows. The aqueous phase (B) containing water was added to oil phase (A) containing sunscreen active ingredient, volatile silicone emulsifier and alcohol using an Eppenbach Homomixer. Mixing was continued for 30 minutes to form a thin water-in-oil emulsion having an average particle size of less than 1 micron. When the sunscreen emulsion of the invention produced as described above was applied to skin, the water and volatile silicone evaporated off leaving a film of sunscreen agent on the skin which was resistant to water and perspiration, but was removable by washing with soap.

EXAMPLE 2

A stable thin water-in-oil sunscreen emulsion in accordance with the present invention, which can be sprayed onto the skin by means of an aerosol or non-aerosol skin treatment system was prepared as described below.

In the formulation, a composition as described in Example 1 (85 parts by weight) is mixed with propellant (15 parts by weight) such as butane and/or propane to form an aerosol composition.

In a second formulation, the composition of Example 1 is employed in a non-aerosol pump spray.

EXAMPLE 3

A moisturizer formulation which includes the delivery system of the invention, having the following composition is prepared as described below.

| Ingredient | | Parts by Weight |
|---|---|---|
| (A) | Oil phase | |
| | Cyclomethicone (D5)-(volatile silicone) (decamethylcyclopentasiloxane) | 15 |
| | Dioleyl methyl glucaside (emulsifier) | 3 |
| | Ethyl alcohol | 20 |
| (B) | Aqueous phase | |
| | Deionized water | 76 |
| | Glycerin (humectant) | 10 |

The moisturizer formulation of the invention is prepared as follows.

The aqueous phase (B) containing water, and glycerin is added to oil phase (A) containing volatile silicone emulsifier using an Eppenbach Homomixer. Mixing is continued for 30 minutes until a thin water-in-oil emulsion forms having an average particle size of less than 1 micron.

When the moisturizer emulsion of the invention produced as described above was applied to skin, the water and volatile silicone evaporated off leaving a moisturizing film on the skin which was resistant to water and perspiration, but was removable by washing with soap.

EXAMPLE 4

A pre-electric shave lotion which includes the delivery system of the invention, having the following composition is prepared as described below.

| Ingredient | | Parts by Weight |
| --- | --- | --- |
| (A) | Oil phase | |
| | Finsolv TN C$_{12-15}$ alcohol benzoate (emollient) | 3 |
| | Cyclomethicone (D$_5$)-(volatile silicone) (decamethylcyclopentasiloxane) | 15 |
| | Dioleyl methyl glucaside (emulsifier) | 3 |
| | Ethyl alcohol | 20 |
| (B) | Aqueous phase | |
| | Deionized water | 76 |

The pre-electric shave lotion of the invention is prepared as follows.

The aqueous phase (B) containing water is added to oil phase (A) containing emollient, alcohol, volatile silicone and emulsifier using an Eppenbach Homomixer. Mixing is continued for 30 minutes until a thin water-in-oil emulsion is formed having an average particle size of less than 1 micron.

When the pre-shave emulsion of the invention produced as described above is applied to skin, the water and volatile silicone evaporate off leaving a film of emollient on the skin which is resistant to water and perspiration, but is removable by washing with soap.

EXAMPLE 5

A thin water-in-oil after-shave emulsion formulation, which includes the delivery system of the invention, having the following composition is prepared as described below.

| Ingredient | | Parts by Weight |
| --- | --- | --- |
| (A) | Oil phase | |
| | C$_{12-15}$ alcohol benzoate | 3 |
| | Cyclomethicone (D$_5$)-(volatile silicone) (decamethylcyclopentasiloxane) | 15 |
| | Dioleyl methyl glucaside (emulsifier) | 3 |
| | Ethyl alcohol | 20 |
| | Fragrance | 10 |
| (B) | Aqueous phase | |
| | Deionized water | 76 |

The after-shave formulation of the invention was prepared as follows.

The aqueous phase (B) containing water was added to oil (A) containing alcohol, fragrance, emollient, volatile silicone and emulsifier using an Eppenbach Homomixer. Mixing is continued for 30 minutes until a thin water-in-oil emulsion is formed having an average particle size of less than 1 micron.

When the after-shave emulsion of the invention produced as described above is applied to skin, the water and volatile silicone evaporated off leaving a film of fragrance oil and emollient on the skin which is resistant to water and perspiration, but was removable by washing with soap.

EXAMPLE 6

A thin water-in-oil cologne emulsion in accordance with the present invention is prepared as described in Example 5 except that 25 parts of ethyl alcohol and 25 parts fragrance are employed.

What is claimed is:

1. A sunscreen composition consisting essentially of a thin water-in-volatile silicone emulsion having a viscosity of less than 10 centipoises, which consists essentially of an interior aqueous phase containing from about 40 to about 85% by weight water; and an exterior silicone phase consisting essentially of from about 5 to about 40% by weight of a volatile silicone, and from about 1 to about 10% by weight of an emulsifier therefor said emulsifier comprising a non-ionic lipophilic low HLB emulsifier having a hydrophilic-lipophilic balance of less than about 7, wherein said emulsifier is selected from the group consisting of dioleyl methyl glucaside, glyceryl monoisostearate, triglyceryldiisostearate, polyethylene glycol (22) dodecyl polymer, triglyceryl diisostearate, sorbitan monooleate, polyglyceryl-2-sesquioleate, sorbitan diisostearate, and mixtures of any two or more thereof, all of said % by weight being based on the total weight of said water-in-volatile silicone emulsion, and from about 1 to about 15% by weight based on the weight of the total sunscreen composition of a sunscreen agent, which sunscreen agent is part of said silicone phase, said sunscreen composition being free of silicon block polymers or copolymers.

2. The composition as defined in claim 1 wherein said sunscreen agent is octyldimethyl-p-aminobenzoic acid, 2-hydroxy-4-methoxybenzophenone (benzophenone 3), octylmethoxycinnamate or mixtures thereof.

3. The composition as defined in claim 1 wherein said silicon phase includes from about 10 to about 30% by weight alcohol.

4. The composition as defined in claim 3 wherein said alcohol is ethanol, isopropanol or mixtures thereof.

5. The composition as defined in claim 1 wherein said emulsifier has a hydrophilic-lipophilic balance of within the range of from about 3 to about 7.

6. The composition as defined in claim 1 wherein said emulsifier is present in an amount of within the range of from about 1 to about 5% by weight based on the total weight of the water-in-volatile silicone emulsion.

7. The composition as defined in claim 1 wherein said emulsifer is dioleyl methyl glucaside.

8. The composition as defined in claim 1 wherein said volatile silicone is present in an amount within the range of from about 10 to about 25% by weight based on the total weight of the water-in-volatile silicone emulsion.

9. The composition as defined in claim 1 wherein said volatile silicone is octamethylcyclotetrasilocane, decamethylcyclopenta-siloxane or hexmethyldisiloxane.

10. The composition as defined in claim 1 wherein the volatile silicone is employed in a weight ratio to the emulsifier of within the range of from about 0.5:1 to about 40:1.

11. The composition as defined in claim 1 wherein said aqueous phase includes from about 40 to about 70 by weight water based on the total weight of the water-in-volatile silicone emulsion.

12. The composition as defined in claim 3 wherein said alcohol is present in an amount of less than 15% by weight and said aqueous phase further includes one or more preservatives in an amount within the range of from about 0.5 to about 2% by weight based on the total weight of the delivery system.

13. The composition as defined in claim 12 wherein said preservative is methyl paraben, propyl paraben, butyl paraben, imidazolidinyl urea, dimethyldimethoyl hydantoin or mixtures of any two or more thereof.

14. The composition as defined in claim 1 wherein said silicone phase is comprised of decamethylcyclopentasiloxane as the volatile silicone and dioleyl methyl glucaside as the emulsifier.

15. The composition as defined in claim 1 wherein said aqueous phase includes a humectant.

16. The composition as defined in claim 1 further including one or more fragrance oils, moisturizers, emollients, and/or humectants.

* * * * *

UNITED STATES PATENT AND TRADEMARK OFFICE
CERTIFICATE OF CORRECTION

PATENT NO. : 4,563,346

DATED : January 7, 1986

INVENTOR(S) : George E. Deckner

It is certified that error appears in the above-identified patent and that said Letters Patent is hereby corrected as shown below:

```
Column 2, line 21, "provide" should read --provides--.
Column 2, line 41, "oil-in-water" should read --water-in-oil--.
Column 2, line 51, "susbstantially" should read
  --substantially--.
Column 6, line 14, after "silicone" insert a comma (,).
Column 8, line 36, "silicon" should read --silicone--.
```

Signed and Sealed this

Eleventh Day of November, 1986

*Attest:*

DONALD J. QUIGG

*Attesting Officer*      *Commissioner of Patents and Trademarks*